United States Patent
Shieh et al.

(10) Patent No.: US 8,574,893 B2
(45) Date of Patent: Nov. 5, 2013

(54) NUCLEIC ACID CLEAVAGE COMPLEX AND METHOD FOR USING THE SAME

(75) Inventors: Dar-Bin Shieh, Tainan (TW); Ying-Ying Li, Kaohsiung (TW); Hung-Ching Lu, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 13/288,531

(22) Filed: Nov. 3, 2011

(65) Prior Publication Data

US 2012/0123107 A1 May 17, 2012

(30) Foreign Application Priority Data

Nov. 17, 2010 (TW) .............................. 99139538 A
Sep. 26, 2011 (TW) ............................ 100134657 A

(51) Int. Cl.
*C12Q 1/68* (2006.01)
*C12M 1/38* (2006.01)
*C12M 3/00* (2006.01)
*C07H 21/02* (2006.01)
*C07H 21/04* (2006.01)

(52) U.S. Cl.
USPC ....... 435/287.2; 435/6.1; 536/23.1; 536/24.3; 536/25.3; 977/773; 977/810; 977/902

(58) Field of Classification Search
USPC ............. 435/6.1, 287.2; 536/23.1, 24.3, 25.3; 977/773, 810, 902
See application file for complete search history.

(56) References Cited

U.S. PATENT DOCUMENTS

2003/0148391 A1* 8/2003 Salafsky ................. 435/7.2

OTHER PUBLICATIONS

Shen et al, Development of a Magnetic Nanoparticle-Based Artificial Cleavage Reagent for Site-Selective Cleavage of Single-Stranded DNA, 2007, Chem. Mater., 19, 3090-3092.*
Shen et al, Supporting information, 2007, Chem. Mater., p. 1-6.*
Shen et al, Primary ODN hairpin structure, data sheet [www.idt.dna.com; p. 1, printed Oct. 26, 2012).*
Tsai et al, The down regulation of target genes by photo activated DNA nanoscissors, 2010, Biomaterials 31, 6545-6554.*
Shieh et al, SPIE Optics+Photonics conference, Aug. 2010, pp. 1-604.*
Anthony et al, A Molecular Beacon Strategy for Real-Time Monitoring of Triplex DNA Formation Kinetics, 2002, Antisense & Nucleic Acid Drug Development 12:145-154.*
D. Praseuth, A.L. Guieysse, and C. Helene; Triple Helix Formation and the Antigene Strategy for Sequence-Specific Control of Gene Expression; Biochimica et Biophysica Acta 1489; Jul. 2, 1999; p. 181-206; 1999 Elsevier Science B.V.
Jih Ru Hwu, Chun Chieh Lin, Shin Hsien Chuang, Ke Yung King, Tzu-Rong Su, and Shwu-Chen Tsay; Aminyl and Iminyl Radicals from Arylhydrazones in the Photo-Induced DNA Cleavage; Bioorganic & Medicinal Chemistry 12; Apr. 10, 2004; p. 2509-2515; 2004 Elsevier Ltd.

(Continued)

*Primary Examiner* — Narayan Bhat
(74) *Attorney, Agent, or Firm* — Bacon & Thomas, PLLC

(57) ABSTRACT

A nucleic acid cleavage complex is disclosed, which includes: a nanoparticle, a nucleic acid cleavage reagent, and a polynucleotide chain specifically recognizing a sequence of a target nucleic acid and having a first terminal and a second terminal opposite to the first terminal, wherein the first terminal is connected to the nanoparticle, the second terminal is connected to the nucleic acid cleavage reagent, and the first terminal sequence and the second terminal sequence are base-paired to make the polynucleotide chain form a hairpin. Also, a method for using the nucleic acid cleavage complex is also disclosed.

14 Claims, 11 Drawing Sheets

(56) References Cited

OTHER PUBLICATIONS

Chiau-Yuang Tsai, Al-Li Shiau, Pai-Chiao Cheng, Dar-Bing Shieh, Dong-Hwang Chen, Chen-His Chou, Chen-Sheng Yeh, and Chao-Laing Wu; A biological Strategy for Fabrication of Au/EGFP Nanoparticle Conjugates Retaining Bioactivity; Nano Letters 2004; May 25, 2004; p. 1209-1212; vol. 4, No. 7; 2004 American Chemical Society.

T. Pellegrino, R.A. Speriling, A.P. Alivisatos, and W.J. Parak; Gel Electrophoresis of Gold-DNA Nanoconjugates; Journal of Biomedicine and Biotechnology; Dec. 13, 2007; p. 1-9; vol. 2007; Hindawi Publishing Corporation.

Ming-Hua Hsu, Thainashmuthu Josephrajan, Chen-Sheng Yeh, Dar-Bin Shieh, Wu-Chou Su, and Jih-Ru Hwu; Novel Arylhydrazone-Conjugated Gold Nanoparticles with DNA-Cleaving Ability: The First DNA-Nicking Nanomaterial; Bioconjugate Chem, 2007; Oct. 23, 2007; p. 1709-1712; vol. 18; 2007 American Chemical Society.

* cited by examiner

```
SEQUENCE LISTING

<160> NUMBER OF SEQ ID NOS: 2

<210> SEQ ID NO 1
<211> LENGTH: 32
<212> TYPE: DNA
<213> ORGANISM: Artificial
<220> FEATURE:
<223> OTHER INFORMATION: Synthesized DNA
<220> FEATURE:
<221> NAME/KEY: stem_loop
<222> LOCATION: (1)..(32)

<400> SEQUENCE: 1
ccaccgtgtt gttggggtgt gggttgtggt gg                                    32

<210> SEQ ID NO 2
<211> LENGTH: 33
<212> TYPE: DNA
<213> ORGANISM: Artificial
<220> FEATURE:
<223> OTHER INFORMATION: Synthesized DNA
<220> FEATURE:
<221> NAME/KEY: stem_loop
<222> LOCATION: (1)..(33)

<400> SEQUENCE: 2
ccaccagtgt tgttggggtg tgggttgtgg tgg                                   33
```

NUCLEIC ACID CLEAVAGE COMPLEX AND METHOD FOR USING THE SAME

CROSS REFERENCE TO RELATED APPLICATION

This application claims the benefits of the Taiwan Patent Application Ser. Nos. 99139538 and 100134657, respectively filed on Nov. 17, 2010 and Sep. 26, 2011, the subject matter of which is incorporated herein by reference.

BACKGROUND OF THE INVENTION

1. Field of the Invention

The present invention relates to a nucleic acid cleavage complex and method for using the same and, more particularly, to a nucleic acid cleavage complex which exhibits high specificity to its target nucleic acid and method for using the same.

2. Description of Related Art

In the early stage of development of the technique for cleaving nucleic acid, the action of the chemically synthesized cleavage reagents occurred randomly and uncontrollably on the nucleic acid. However, as the technique improves, the sequence-specific nucleic acid cleavage tools such as restriction enzymes have been recently developed. Accordingly, the abovementioned problems can be partially solved. Thus, the technique of cleaving nucleic acid can be widely applied in medical and biogenetic engineering techniques such as plasmid recombination, gene transformation, and gene mapping analysis so as to improve the efficiency of the related techniques.

The length of the sequence recognized by the aforesaid restriction enzymes is generally about 4-8 base pairs (bp). However, because several recognized sequences with the length mentioned above are repeatedly found in a long DNA fragment, the sequence-specific nucleic acid cleavage tools capable of recognizing the sequence with the length of 4-8 by still can not accomplish specific cleavage on the particular site of DNA. Accordingly, it is difficult to meet the requirement of advanced medical and biogenetic engineering techniques. Therefore, it is desirable to develop a nucleic acid cleavage tool, and this tool can cleave the nucleic acid inside or outside the cells and will not randomly attack unspecific sequences. Furthermore, it is expected that this tool can specifically and simultaneously cleave several target nucleic acids or genes, and to overcome the defects of the restriction enzymes such as limitation of sequence length, and inconvenience of the needs for various buffer conditions such that the medical and biogenetic engineering techniques can be promoted further.

SUMMARY OF THE INVENTION

The object of the present invention is to provide a nucleic acid cleavage complex. The specific cleavage to the sequence of the target nucleic acid can be carried out by the activation of the nucleic acid cleavage reagent in the nucleic acid cleavage complex of the present invention. Besides, the complex won't attack the nucleic acid of the sequences other than those of the target nucleic acid. Thus, the sequences other than that of the target nucleic acid do not be damaged.

To achieve the object, the nucleic acid cleavage complex of the present invention includes: a nanoparticle; a nucleic acid cleavage reagent; and a polynucleotide chain which specifically recognizes a sequence of a target nucleic acid, and has a first terminal and a second terminal opposite to the first terminal, wherein the first terminal is connected to the nanoparticle, the second terminal is connected to the nucleic acid cleavage reagent, and the first terminal sequence and the second terminal sequence are base-paired to make the polynucleotide chain form a hairpin.

In the aforesaid nucleic acid cleavage complex of the present invention, the length of the polynucleotide chain is not particularly limited, and it can be in a range of about 10-30 nucleotides (nt), particularly for example, 15, 20, 25, and 35 nt. Besides, the polynucleotide chain mainly contains three sections. One end of the first section is the first terminal that is connected to the nanoparticle, and the other end thereof is connected to the second section. One end of the third section is the second terminal that is connected to the nucleic acid cleavage reagent, and the other end thereof is connected to the second section. Hence, the connection manner is "the nanoparticle-the first section-the second section-the third section-the nucleic acid cleavage reagent" in order. Besides, the sequence of the third section is complementary to partial sequence of the first section to make the polynucleotide chain form a hairpin. Because the length of the complementary sequences between the first and third sections will influence unfolding of the polynucleotide chain and the following specific recognition to the target nucleic acid, the length of the complementary sequences between the first and third sections requires to be controlled appropriately, and for example, it can be 3-10 base pairs (bp). For instance, the sequence length of the first section can be approximately 1-25 nt, and those of the second and third sections can be about 5-80 nt and 1-25 nt, respectively. Preferably, the sequence length of the first section can be approximately 6-20 nt, and those of the second and third sections can be about 15-70 nt and 6-20 nt, respectively.

The term "specific recognition" described herein refers to the base pairing based on the rules of Watson-Crick base pairing and non-Watson-Crick base pairing such as Hoogsteen base pairing and wobble base pairing. In the present invention, the base in each nucleotide of the polynucleotide chain is paired with the corresponding base in each nucleotide of the target nucleic acid to form hydrogen bonds according to the rules of Hoogsteen base pairing or Non-Hoogsteen base pairing. For example, if there are bases such as purines and pyrimidines in the polynucleotide chain of the present invention, the corresponding bases of the target double-stranded DNA can be purines such as adenine, guanine, and modified derivatives thereof. If there are only pyrimidines in the polynucleotide chain of the present invention, the corresponding bases of the target double-stranded DNA can be purines such as adenine and protonated guanine. Accordingly, if the pairing can not occur to form hydrogen bond between the polynucleotide chain of the present invention and certain nucleic acid, the recognition can not be accomplished and thus the abovementioned recognition is named as the specific recognition.

Furthermore, since the polynucleotide chain of the present invention can be paired with the target nucleic acid in accordance with the pairing rule depicted above, the target nucleic acid can be single-stranded or double-stranded nucleic acid, RNA or DNA, natural or artificially synthesized nucleic acid, and so forth. Particularly, single-stranded RNA or double-stranded DNA prepared by purification from natural products, polymerase chain reaction (PCR), chemical synthesis, or other conventional manners can be the target nucleic acid. Accordingly, after the polynucleotide chain of the present invention specifically recognizes the target nucleic acid, double-stranded or triple-stranded helix nucleic acid can form. If the triplex nucleic acid forms, the pairing of the polynucleotide chain mainly occurs in the major groove of the duplex target nucleic acid. This also indicates that the polynucleotide chain of the present invention functions as triplex-forming oligonucleotide (TFO) chain.

Besides, the sequence length of the target nucleic acid is not also limited. In general, the region of the target nucleic acid specifically recognized by the polynucleotide chain is in the sequence length of about 10-30 nt, and preferably in the length of about 11-25 nt. Because the polynucleotide chain of the present has to recognize the target nucleic acid specifically, partial sequences of the polynucleotide chain and the target nucleic acid have to be complementary, i.e. are able to be paired. Thus, the recognition can be accomplished. Furthermore, if the region that specifically recognizes the target nucleic acid in the polynucleotide chain is located in the second section between the first and second terminals, the location of the target nucleic acid cleaved by the nucleic acid cleavage reagent is several nucleotides away from the recognized region because the nucleic acid cleavage is connected to the third section at the second terminal of the polynucleotide chain. Accordingly, the cleavage location of the target nucleic acid can be predetermined.

Moreover, the terms "cleave" and "cleavage" described herein mean that the external force or action causes a gap or nick between two neighboring nucleotides in continuous nucleic acid and results in no original function of the cleaved nucleic acid.

In the nucleic acid cleavage complex of the present invention, single nanoparticle can be connected with 30-100 polynucleotide chains. The single nanoparticle is not limited to be connected with only one species of the polynucleotide chains and can be simultaneously connected with several species thereof to achieve specific recognition to the other regions of the target nucleic acid or the other corresponding target nucleic acid. Accordingly, if several kinds of the polynucleotide chains are connected to the nanoparticle in the nucleic acid cleavage complex, specific recognition to single or multiple different target nucleic acids can occur. After the nucleic acid cleavage reagent is activated, the cleavage of the target nucleic acid can be carried out.

Moreover, the kinds, shapes, particle sizes, and materials of the nanoparticle are not limited particularly. Suitable nanoparticle can be selected according to the requirements for applications or the method for preparing the nucleic acid cleavage complex. Metals (ex. indium, titanium, copper, gold, silver, iron, cobalt, aluminum, palladium, platinum, zinc, tin, chromium, and nickel), magnetic materials with paramagnetism that can be attracted or repelled by an external magnetic field and beneficial to control or collect the nucleic acid cleavage complex of the present invention (ex. ferric oxide and nickel oxide), semiconductors (ex. cadmium sulfide, cadmium selenide, and cadmium sulfide and cadmium selenide encompassed with zinc sulfide), organic substances (ex. Si and silicon oxide), organic polymers (ex. poly(lactide-co-glycolide) (PLGA) and polyethylene glycol (PEG)), or a combination thereof are exemplified as the materials of the nanoparticle. Nanorods, isotropic nanoparticles (ex. solid or hollow spherical nanoparticles), anti-isotropic nanoparticles (ex. anisotropic conical, rectangular, or rhombic nanoparticles), dendrimers, and composite nanoparticles (ex, core-shell nanoparticles such as $SiO_2$@Au) are exemplified as the kinds of the nanoparticle. The average particle size of the nanoparticles generally ranges approximately from 1 to 100 nm, and preferably from 10 to 30 nm.

In the nucleic acid cleavage complex mentioned above, the method for connecting the polynucleotide chain to the nanoparticle is not particularly limited. For example, the first terminal of the polynucleotide chain can be connected to the nanoparticle by a functional group (ex. thioether), a monomer (ex. ethylene glycol), a polymer (ex. poly(ethylene glycol) and so forth. Also, the method for connecting the nucleic acid cleavage reagent to the polynucleotide chain is not limited particularly. For instance, the polynucleotide chain is modified to form amines at the second terminal, and then covalently bonded to the nucleic acid cleavage reagent by the amines.

Furthermore, the kinds of the nucleic acid cleavage reagent are not limited particularly, and can be, for example, a photoexcited nucleic acid cleavage reagent particularly such as hydrazone, azidoproflavine, azidophenacyl, azido derivatives, ellipticine derivatives, and indocyanine green (ICG) derivatives. The nucleic acid cleavage reagent can be excited, for example, by visible spectrum, UV, or near-IR. The nucleic acid cleavage reagent used in the present invention is an ICG derivative belonging to symmetric carbocyanine group, named as cypate that can be excited by near-IR, i.e., NIR cyanine dyes. Water, erythrocytes, or hematin inside bioorganisms have the minimal absorption at about 800 nm. The irradiation at 800 um exhibits relatively deep penetration in the bioorganisms, and can be employed as a light source for the thermal treatment and for noninvasive monitoring of deep tissues (Ralph Weissleder. A clearer vision for in vivo imaging. Nature biotechnology 19; 316-317 (2001)). Accordingly, when the nucleic acid cleavage reagent is not activated, the conformation of the hairpin polynucleotide chain makes the activation energy of the nucleic acid cleavage reagent be absorbed by surface plasmon resonance (SPR) of the nanorod. The quenching effect of the activation energy occurs, and thus the cleavage of the nucleic acid cannot be carried out. Only when the hairpin polynucleotide chain recognizes the specific sequence and is unfolded into a linear line, the nucleic acid cleavage reagent is distant from SPR of the nanorod and thus activated to cleave the target nucleic acid. In addition, the nucleic acid cleavage reagent of the present invention requires to be selected according the kind of the target nucleic acid. For example, if the target nucleic acid to be cleaved is DNA, the nucleic acid cleavage reagent has to be able to cleave DNA.

Anther object of the present invention is to provide a method for using the nucleic acid cleavage complex mentioned above. When the nucleic acid cleavage complex functions in the absence of the target nucleic acid, the nucleic acid cleavage reagent can not be easily exposed and randomly excited even if the nucleic acid cleavage reagent is irradiated or activated by the other manners. Because the polynucleotide chain keeps the hairpin shape, the nucleic acid cleavage reagent is very close to the nanoparticle. The activation energy of the nucleic acid cleavage reagent can be absorbed by SPR of the nanoparticle and then quenched. Therefore, the nucleic acid cleavage reagent can be safely exposed to non-target nucleic acid and keeps inactive. Only when the hairpin polynucleotide chain contacts the target nucleic acid, the specific recognition occurs between the hairpin polynucleotide chain and the target nucleic acid and thus the hairpin polynucleotide chain is unfolded to pair with the target nucleic acid. Meanwhile, the nucleic acid cleavage reagent is just exposed. When the irradiation of a suitable wavelength is performed, the cleavage is carried out to permanently inhibit the expression of the target nucleic acid. In addition, the conformation of the hairpin polynucleotide chain can effectively protect the photoexcited nucleic acid cleavage reagent from being degraded in the bioorganisms and enhance the efficiency of the specific cleavage.

The method for using the nucleic acid cleavage complex of the present invention includes the following steps: providing a target nucleic acid and a nucleic acid cleavage complex which comprises: a nanoparticle; a nucleic acid cleavage reagent; and a polynucleotide chain which specifically recognizes a sequence of a target nucleic acid, and has a first terminal and a second terminal opposite to the first terminal, wherein the first terminal is connected to the nanoparticle, the second terminal is connected to the nucleic acid cleavage reagent, and the first terminal sequence and the second terminal sequence are base-paired to make the polynucleotide chain form a hairpin; allowing the nucleic acid cleavage complex to contact the target nucleic acid, wherein the polynucleotide chain of the nucleic acid cleavage complex specifically recognize the sequence of the target nucleic acid; and activating the nucleic acid cleavage reagent of the nucleic acid cleavage complex to cleave the sequence of the target nucleic acid.

For example, when the method of the present invention is performed in a solution in vitro, the nucleic acid cleavage complex functions as a restriction enzyme and can recognize the specific sequence distributed in the solution to achieve the cleavage. Subsequently, a ligase is used to achieve gene or plasmid recombination. In addition, if the method of the present invention is performed on cells in vitro, the nucleic acid cleavage complex distributed in the culture medium will naturally enter the cells (i.e. without external force of an electric field or high-pressure of gas) and cleave the specific recognition sequence. If the specific recognition sequence is not present in the cells, the labeling of the specific gene sequence in the cells cannot be accomplished. Therefore, the screening and treatment of the cancer cell with the mutative specific recognition sequence can be achieved. Accordingly, in the present invention, the nucleic acid cleavage complex and the method using the same is widely applied without any limitation, and can be used in related applications requiring the nucleic acid cleavage such as gene mapping analysis, nucleic acid cleavage in vitro, nucleic acid examination in vitro, gene or plasmid recombination, and phylogenetic identification. It is indicated that the nucleic acid cleavage complex and the method for using the same of the present invention can be used, modified, combined with conventional techniques in the art before or after the target is cleaved.

Besides, the nucleic acid cleavage complex of the present invention can be combined with a pharmaceutically acceptable carrier to form a pharmaceutical composition. If the pharmaceutical composition is formed, the amount of the nucleic acid cleavage complex has to be effective, i.e. sufficient to achieve high specificity of the cleavage to the target nucleic acid. In other words, pharmacological theories such pharmacokinetics and the loss of the nucleic acid cleavage complex under penetration through the cell membrane also need to be considered. The pharmaceutically acceptable carrier can be, for example, mannitol, glucose, microcrystalline cellulose, skimmed milk powder, polyvinyl prrolidone, starch, and a combination thereof. The pharmaceutical composition can be administered according to the conditions, and for example via spray inhalation, topically, by nasal absorption, orally, parentally, via an implanted reservoir, by micro-injection, by gene gun transfection, and a combination thereof. The parental administration includes subcutaneous, intradermal, intravenous, intramuscular, intra-articular, intra-arterial, synovial, and sternal injections or injection methods.

Therefore, in the present invention, the hairpin polynucleotide chain of the nucleic acid cleavage complex can be designed and modified in accordance with various target nucleic acids so as to satisfy customization needs. In other words, based on various target nucleic acid, the nucleic acid cleavage complex is prepared correspondingly. In addition, photons of the specific wavelength can be optically focused on a certain region so as to restrict the area of the gene cleavage.

In conclusion, the nucleic acid cleavage complex and the method for using the same of the present invention can overwhelm the defects that the restriction enzymes have insufficient recognizability to a relatively long nucleic acid sequence and improve practicability of the nucleic acid cleavage techniques. Besides, only one kind of the buffer is required in various sequence cleavages by the nucleic acid cleavage complex. The cleavage by the nucleic acid cleavage complex can be controlled in respect of the synchronicity, locations, and motions by optic apparatus. When the nucleic acid cleavage complex is used, its location can be tracked with development techniques. Hence, the nucleic acid cleavage complex and the method for using the same of the present invention have wide applicability and following benefits. First, the specific cleavage can be carried out on multiple target genes, simultaneously. Second, compared with the restriction enzymes, the complex is not influenced by the sequence length. Third, the complex with relatively small volume can easily enter the cells and their nuclei to carry out the cleavage. Fourth, the permanent damage can be made on the target nucleic acid. Fifth, the photo-regulated cleavage can be integrated with an image-tracking device. Sixth, the location and the applied energy of the cleavage can be precisely controlled by an optic system. Seventh, the hairpin conformation can dramatically improve specificity and efficiency of the cleavage, and reduce the possibility that the chemical cleavage reagent is degraded. Eighth, the irradiation source used for excitation of the reagent is near-IR which is not absorbed relatively by the bioorganisms.

Other objects, advantages, and novel features of the invention will become more apparent from the following detailed description when taken in conjunction with the accompanying drawings.

DETAILED DESCRIPTION OF THE PREFERRED EMBODIMENT

Figure 1A:
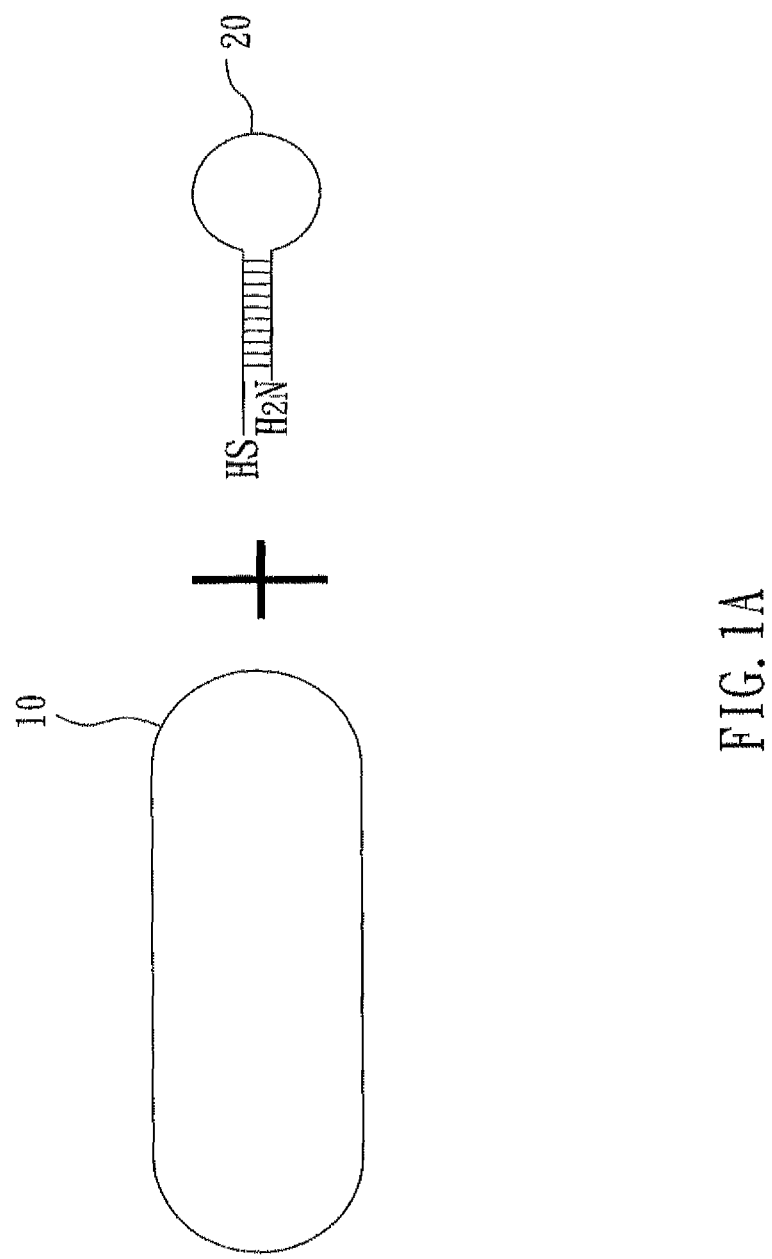
FIGS. 1A to 1C show a flow chart of preparation of the nucleic acid cleavage complex in Example 1 of the present invention.

Because of the specific embodiments illustrating the practice of the present invention, one skilled in the art can easily understand other advantages and efficiency of the present invention through the content disclosed therein. The present invention can also be practiced or applied by other variant embodiments. Many other possible modifications and variations of any detail in the present specification based on different outlooks and applications can be made without departing from the spirit of the invention.

The drawings of the embodiments in the present invention are all simplified charts or views, and only reveal elements relative to the present invention. The elements revealed in the drawings are not necessarily aspects of the practice, and quantity and shape thereof are optionally designed. Further, the design aspect of the elements can be more complex.

EXAMPLE 1

Preparation for a Nucleic Acid Cleavage Complex

Figure 1B:
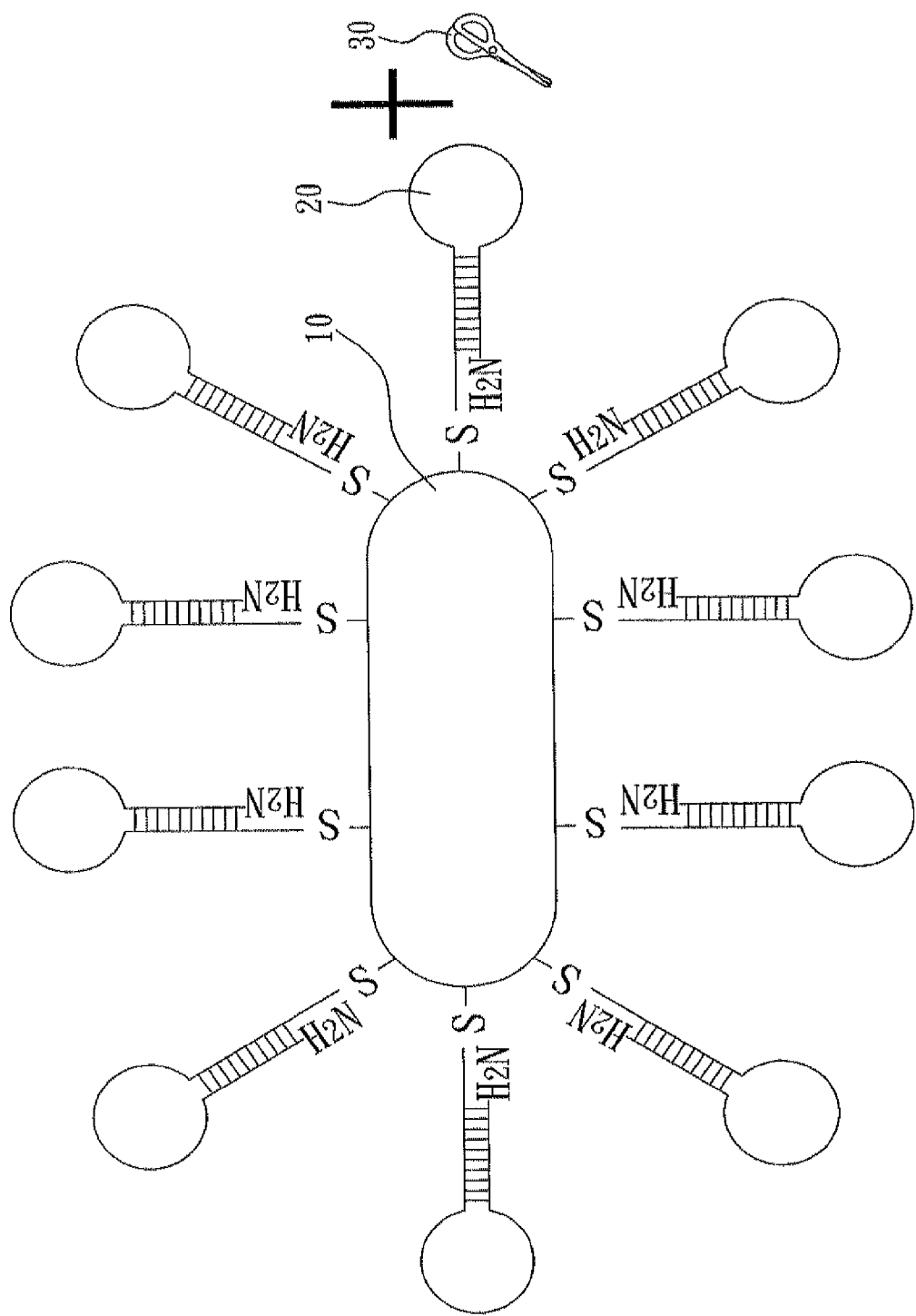
Figure 1C:
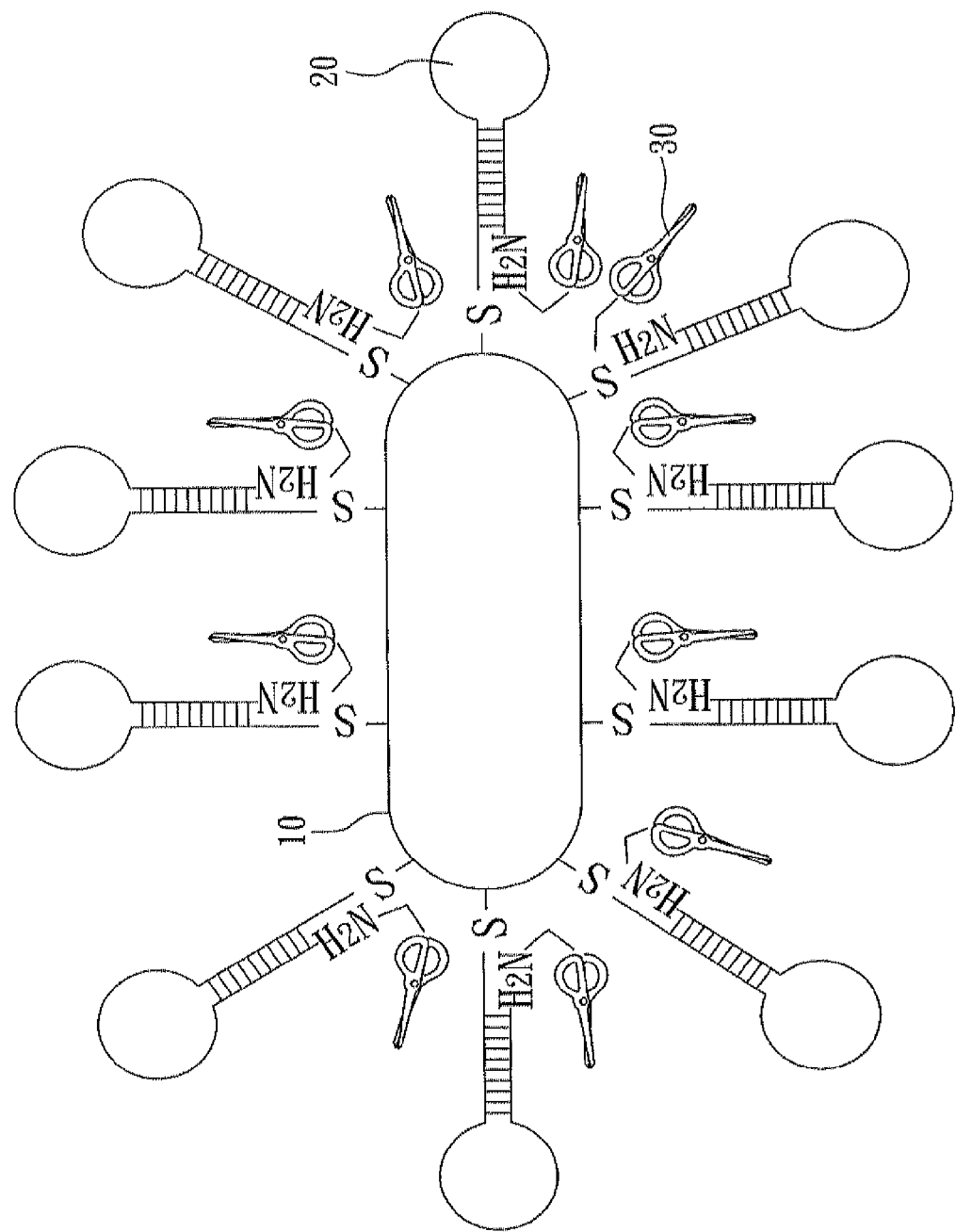

With reference to FIGS. 1A to 1C, there is shown a flow chart of preparing a nucleic acid cleavage complex of the present invention. First, as shown in FIG. 1A, a nanoparticle 10 and a hairpin polynucleotide chain 20 are prepared. In the present example, the nanoparticle 10 is a gold nanorod, and this nanorod can be prepared by seeded-mediated growth (also named as seeding growth approach). In this method, cetyltrimethylammonium bromide (CTAB, 1.822 g) and $AgNO_3$ (60 μL, 100 mM) are added into aqueous $HAuCl_4$ solution (0.5 mM) and then stirred sufficiently. During the strong agitation, ascorbic acid (300 μL, 100 mM) is added and thus $Au^{3+}$ is reduced into $Au^+$. After the strong agitation is kept for five seconds, $NaBH_4$ (20 100 mM) is immediately added. Meanwhile, $Au^+$ is reduced into a zerovalent gold atom and formation of cores and growth of crystals start. After two hours, the reaction is accomplished. $Ag^+$ of $AgNO_3$ and $Br^-$ of CTAB form AgBr solids. These solids are selectively deposited and absorbed on the lattice plane {110} and thus slow the growth of the crystal. Accordingly, the product is a gold nanorod rather than a gold nanoball and the aspect ratio of the nanorod ranges from 3.5 to 4 (J. P. Juste et al., Electric-field-directed growth of gold nanorods in aqueous surfactant solutions. *Adv. Funct. Mater* 14; 571-579 (2004)). Finally, the prepared gold nanorods are scanned at the continuous wavelength from 400 to 1100 nm.

Subsequently, the hairpin polynucleotide chain 20 is prepared. The sequence of the polynucleotide chain 20 is exemplified as SEQ ID NOs. 1 and 2 but not limited thereto, and can be designed according to the requirements. In SEQ ID NO. 1, there are five base pairs at 3'- and 5'-terminals. In SEQ ID NO. 2, there are six base pairs at 3'- and 5'-terminals. These base pairs form the stem of the hairpin polynucleotide chain, and the other unpaired bases form the loop thereof. Referring to the polynucleotide chain 20, its 5'- and 3'-termini are modified into thiol (SH) and amino ($NH_2$), respectively. The abovementioned functional groups are connected with the nucleotides by six carbon atoms which are synthesized by MDbio, Inc. (Taiwan, Taipei). The sequence can be designed according to the following paper: Philippe Simon et al., Targeting DNA with triplex-forming oligonucleotides to modify gene sequence. *Biochimie* 90: 1109-1116 (2008).

Since a gold nanorod is used as the nanoparticle 10 of the present invention, the gold nanorod can be connected with the hairpin polynucleotide chain 20 by known methods in the art. For example, the gold nanorod and the hairpin polynucleotide chain 20 are mixed in a molar ratio of 1:100, and the resultant mixture is evenly stirred for 16 hours. After the thiol of the hairpin polynucleotide chain 20 is oxidized into thioether, the hairpin polynucleotide chain 20 can be covalently linked with the gold nanorod. Posterior to centrifugation at 10000 rcf, the supernatant and the unlinked gold nanorod and hair polynucleotide chain are removed. Then, double deionized water (1 ml) is used to repeat this step. Finally, the centrifugation at the same rotation rate is performed to remove the waste, and the resultant product is dissolved in double deionized water (0.5 ml).

Subsequently, with reference to FIG. 1B, the nucleic acid cleavage reagent 30 is provided for linkage with the 3'-terminal of the polynucleotide chain 20.

With respect to the linkage between the nucleic acid cleavage reagent 30 and the polynucleotide chain 20, it can be achieved by known methods in the art. For example, in the present example, cypate (125 μM) used as the nucleic acid cleavage reagent 30 is mixed with the polynucleotide chain 20 linked to the gold nanorod 10 in a molar ratio of 1:100 and reacted for 16 hours. After centrifugation at 10000 rcf, the supernatant is removed. Double deionized water is used to repeat this step. Finally, the resultant product is dissolved in double deionized water (50 μl).

Figure 2:
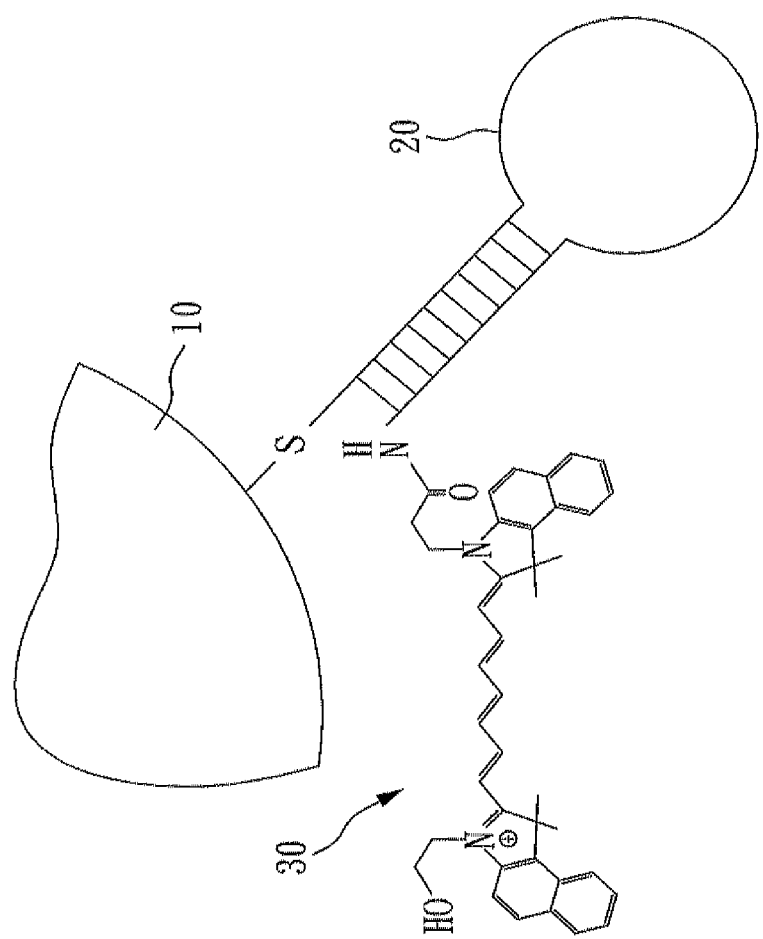
FIG. 2 is a partially enlarged view of FIG. 1C.

The structure of the resultant nucleic acid cleavage complex 1 is shown as FIG. 1C. The linkage between cypate and the hairpin polynucleotide chain 20 is shown as FIG. 2.

EXAMPLE 2

Method for Using the Nucleic Acid Cleavage Complex

With reference to FIGS. 3A to 3E, there is shown a method for using the nucleic acid cleavage complex of the present invention.

Figure 3A:
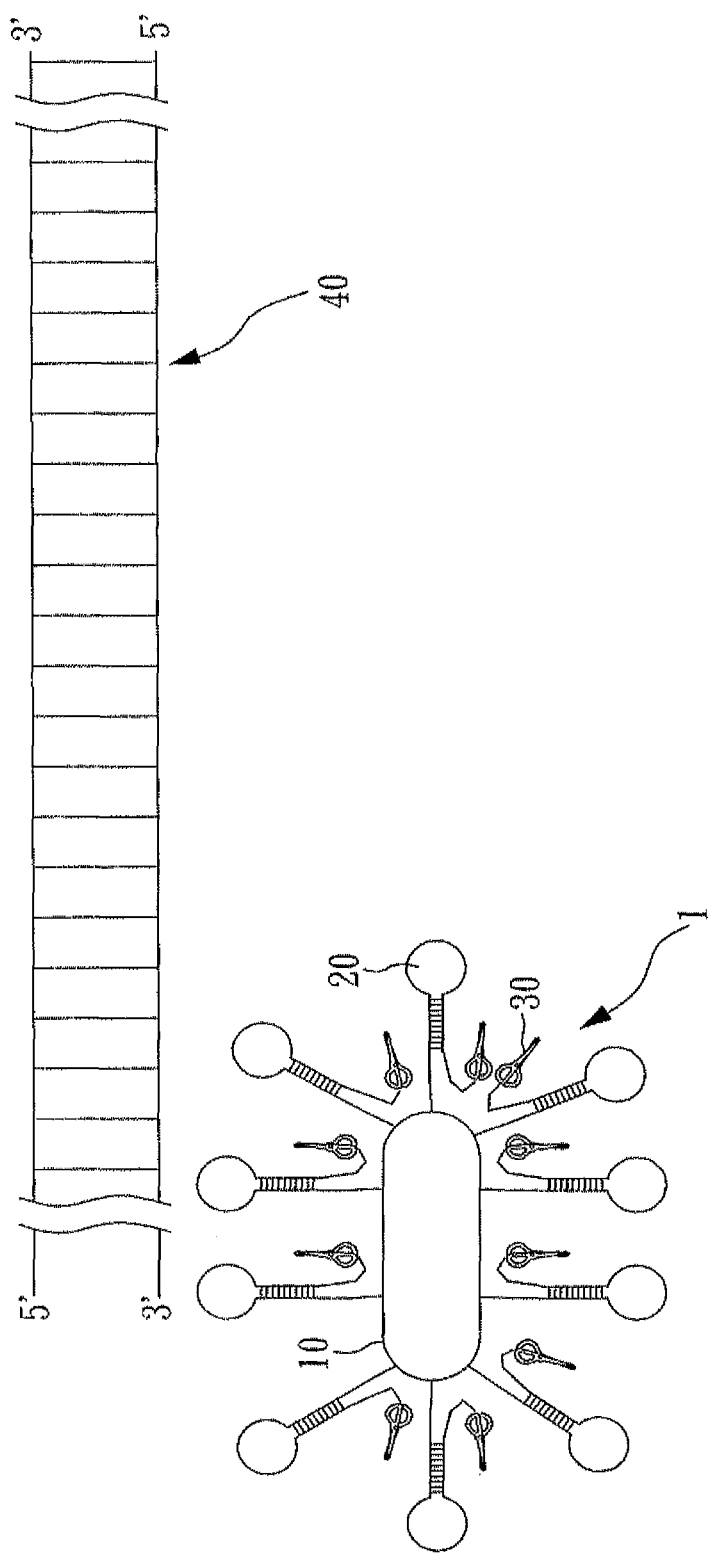
FIGS. 3A to 3E show a flow chart of the method for using the nucleic acid cleavage complex in Example 2 of the present invention.

First, as shown in FIG. 3A, a nucleic acid cleavage complex 1 and a target nucleic acid 40 are provided. The target nucleic acid 40 can be present in a solution and a cell in vitro. The nucleic acid cleavage complex 1 includes: a nanoparticle 10, a nucleic acid cleavage reagent 30, and a polynucleotide chain 20. The polynucleotide chain 20 has a first terminal and a second terminal opposite to the first terminal. The first terminal is connected to the nanoparticle. The second terminal is connected to the nucleic acid cleavage reagent. In addition, the first terminal sequence and the second terminal sequence are base-paired to make the polynucleotide chain form a hairpin.

Figure 3B:
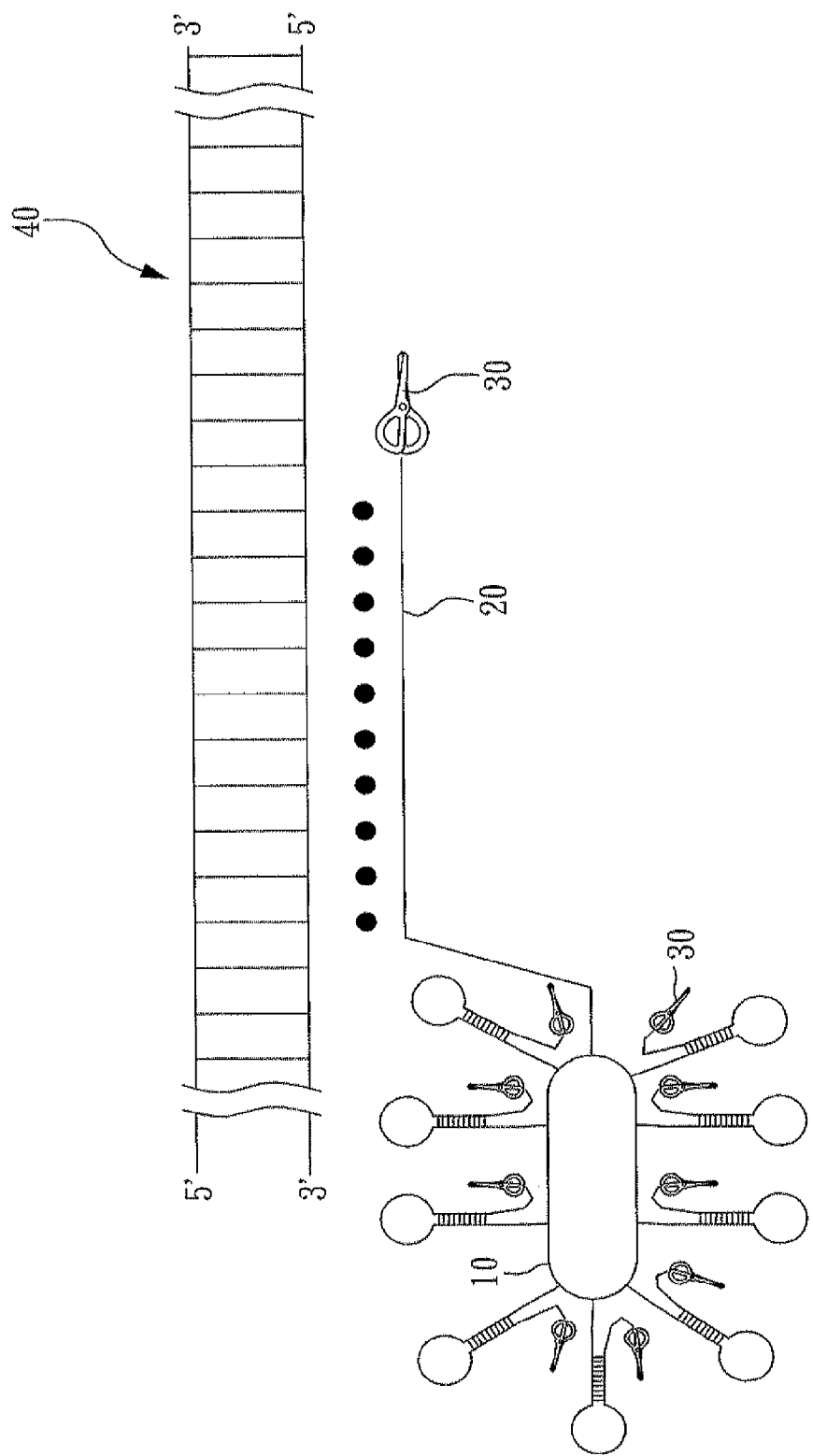

As shown in FIG. 3B, the nucleic acid cleavage complex 1 and the target nucleic acid 40 are evenly mixed. Thus, the nucleic acid cleavage complex 1 contacts the target nucleic acid 40 in a solution or cells. Meanwhile, the polynucleotide chain 20 of the nucleic acid cleavage complex 1 is able to specifically recognize a part of the sequence of the target nucleic acid 40 (as black dots shown in the figure). Because the target nucleic acid 40 is a double-stranded helix, the polynucleotide chain 20 is unfolded and binds to the recognition region of the target nucleic acid 40 to form a triplex structure during the specific recognition.

Figure 3C:
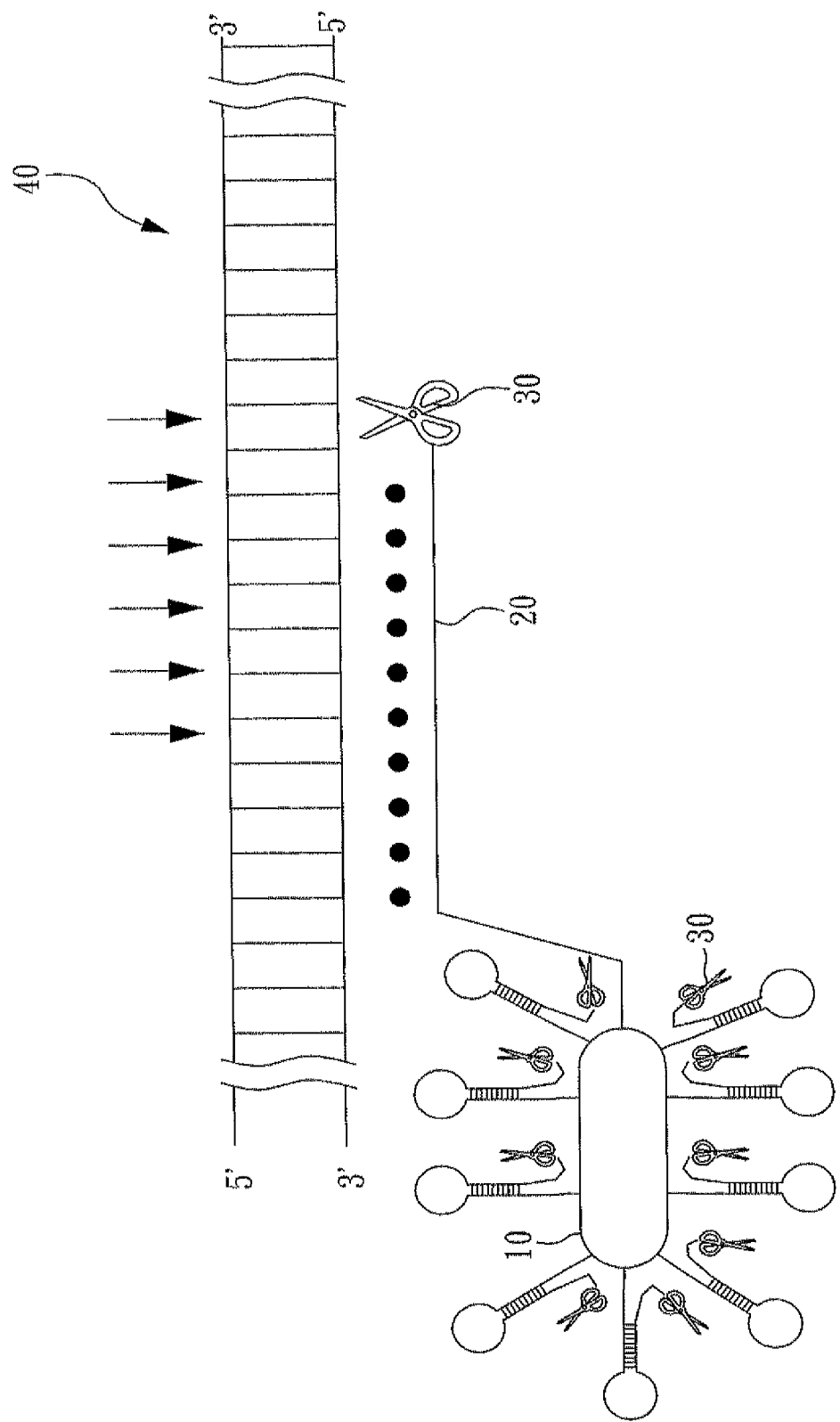

As shown in FIG. 3C, if a photoexcited nucleic acid cleavage reagent is used as the nucleic acid cleavage reagent 30, an irradiation source with a suitable wavelength can be selected to activate the nucleic acid cleavage reagent 30 of the nucleic acid cleavage complex I. For example, if near-IR is used for activation in the present example, the activated nucleic acid cleavage reagent 30 becomes excited and then cleaves the base pairs or neighboring base pairs of the target nucleic acid 40.

Figure 3D:
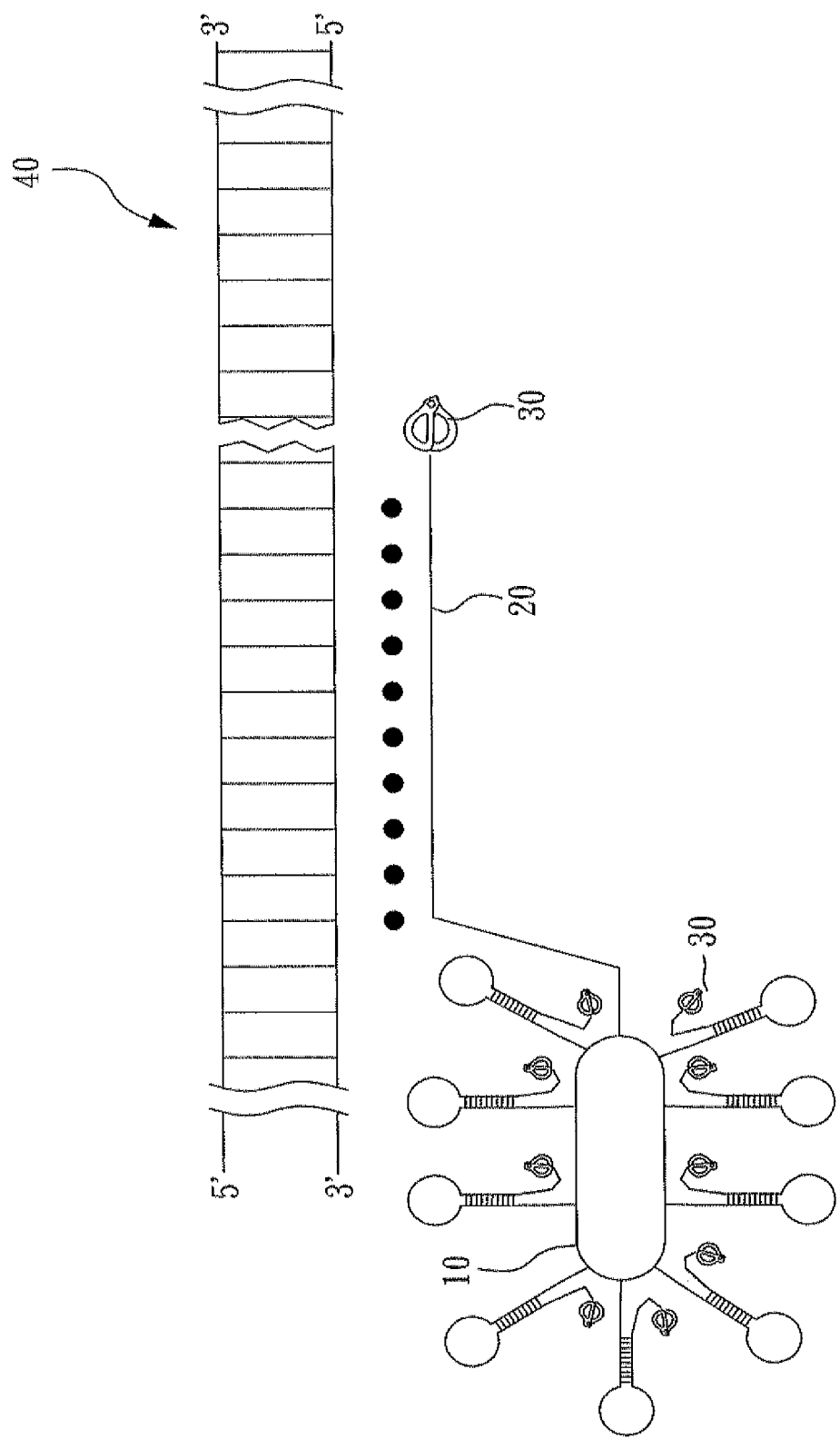

Finally, as shown in FIG. 3D, the cleavage reagent posterior to cleaving the target nucleic acid 40 becomes inactive and unexcited, and the cleaved target nucleic acid 40 loses its function.

Figure 3E:
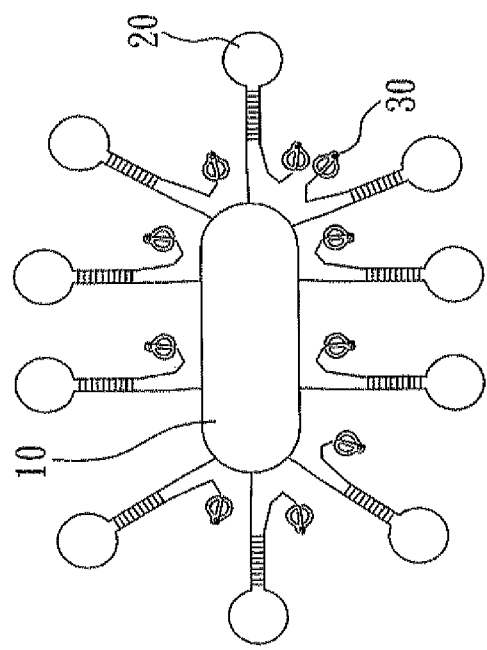

Besides, as shown in FIG. 3E, the nucleic acid cleavage reagent 30 linked to the residue of the polynucleotide chains 30 by which recognition are not carried out on the target nucleic acid 40, is photodegraded and lose activity after irradiation.

TEST EXAMPLE 1

Specific Recognition Test in Vitro

First, construction of a test vector is performed. A full-length plasmid (pGEM®-T Easy) is modified to contain the sequence that is going to be recognized by a hairpin polynucleotide chain, and then named as pST3 test vector. Besides, two hairpin polynucleotide chains (a and b) able to recognize the pST3 test vector and two (c and d) having different scramble sequences in the same order are designed.

Subsequently, the abovementioned vector and four of the hairpin polynucleotide chains are mixed in molar ratios of 1:1000 (see columns 3, 5, 7, and 9 in FIGS. 4) and 1:10000 (see columns 4, 6, 8, and 10 in FIG. 4), and then incubated at 37° C. Finally, the product is analyzed by 12% undenatured polyacrylamide gel according to electrophoretic mobility shift assay (EMSA), so as to check whether the hairpin polynucleotide chains specifically recognize the corresponding sites of the vector.

Figure 4:
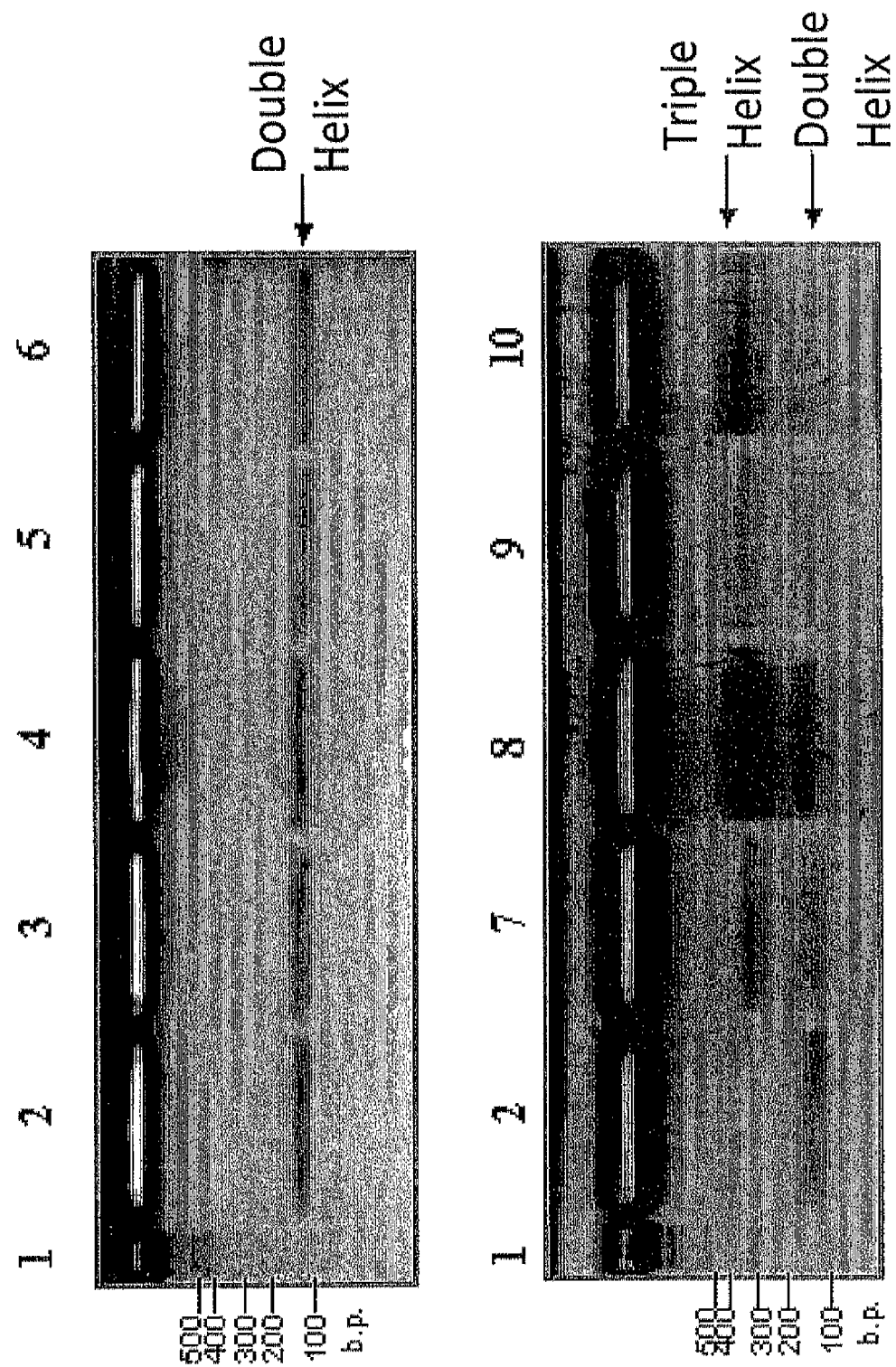
FIG. 4 is an electrophoresis photograph obtained from the specific recognition test in Test Example 1 of the present invention.

The test result is shown in FIG. 4. In FIG. 4, Column 1 represents a molecular weight marker, column 2 represents the test vector, columns 3, 4, 5, and 6 represent the complexes formed from the test vector and the hairpin polynucleotide chains (c and d) having different scramble sequences, and columns 7, 8, 9, and 10 represent the complexes formed from the test vector and the hairpin polynucleotide chains (a and b) able to recognize the test vector. As shown in columns 3, 4, 5, and 6 of FIG. 4, since the hairpin polynucleotide chains (c and d) having the scramble sequences are unable to recognize the recognizable sequence of the test vector, a triple helix can not be found. As shown in columns 7, 8, 9, and 10 of FIG. 4, a triple helix can be found due to specific recognition of the hairpin polynucleotide chains (a and b) to the test vector. This test evidences that the sequence designed in the present invention can achieve the specific recognition to the target gene sequence.

TEXT EXAMPLE 2

DNA Cleavage Test of the Nucleic Acid Cleavage Reagent in vitro

Figure 5:
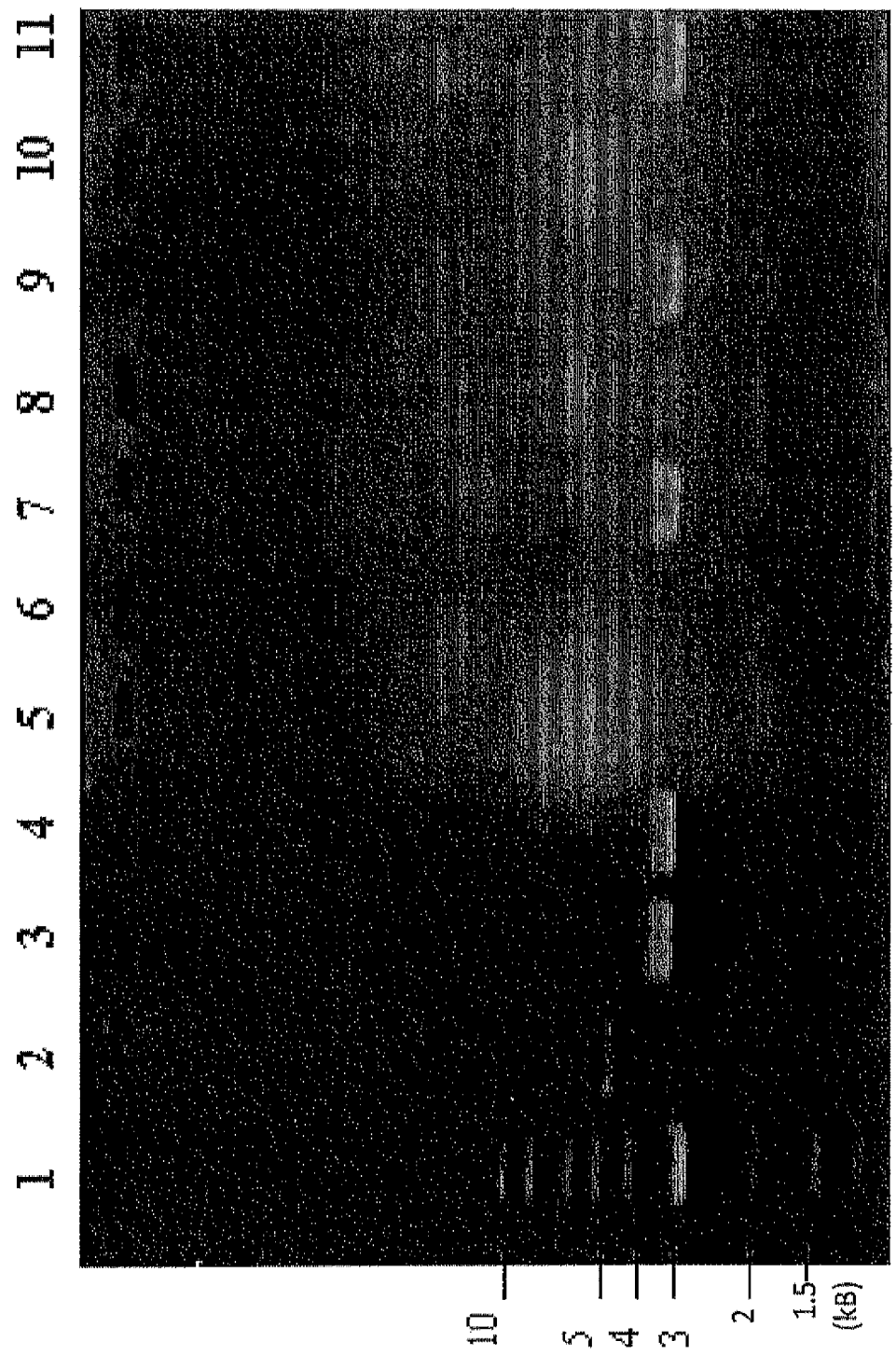
FIG. 5 is an electrophoresis photograph obtained from the in vitro DNA cleavage test of the nucleic acid cleavage reagent in Test Example 2 of the present invention.

First, the pST3 test vector of Test Example 1 is prepared. The abovementioned vector and the nucleic acid cleavage reagent (Cypate) are mixed in a molar ratio of 1:1000. Column 2 of FIG. 5 shows a linear plasmid (Form III plasmid) after the test vector is treated with a restriction enzyme. Columns 3, 4, and 7 of FIG. 5 demonstrate that the test vectors are not cleaved with irradiation for 10 mins (column 3) or without irradiation (columns 4 and 7) and the supercoiled structure (Form I plasmid) remains. Columns 5 and 6 of FIG. 5 show the position of the nucleic acid cleavage reagent (Cypate) in the gel. Columns 8 and 9 of FIG. 5 show that after the mixture containing the test vector and the nucleic acid cleavage reagent is treated with irradiation (column 8) for 5 mins and without irradiation (column 9), the irradiated plasmid is partially cleaved to form nicked open-circular plasmid (Form II plasmid). Columns 10 and 11 of FIG. 5 show that after the mixture containing the test vector and the nucleic acid cleavage reagent is treated with irradiation (column 10) for 10 mins and without irradiation (column 11), the irradiated plasmid is completely cleaved to totally form nicked open-circular plasmid (Form II plasmid). This test also indicates that the nucleic acid cleavage reagent (Cypate) synthesized in the present invention can achieve the DNA cleavage.

Although the present invention has been explained in relation to its preferred embodiment, it is to be understood that many other possible modifications and variations can be made without departing from the scope of the invention as hereinafter claimed.

---

What is claimed is:

1. A nucleic acid cleavage complex, comprising:
a nanoparticle;
a nucleic acid cleavage reagent, wherein said nucleic acid cleavage reagent is photo-excitable by visible light, ultraviolet light, and near infrared; and
a polynucleotide chain which specifically recognizes a sequence of a target nucleic acid, and has a first terminal sequence and a second terminal sequence opposite to the first terminal sequence, wherein the first terminal sequence is connected to the nanoparticle, the second terminal sequence is connected to the nucleic acid cleavage reagent, and the first terminal sequence and the second terminal sequence are base-paired to make the polynucleotide chain form a hairpin.

2. The nucleic acid cleavage complex of claim 1, wherein the average particle size of the nanoparticle is in a range of 1-100 nm.

3. The nucleic acid cleavage complex of claim 1, wherein the length of the polynucleotide chain is in a range of 10-30 nucleotides.

4. The nucleic acid cleavage complex of claim 1, wherein the length of the base-paired sequences between the first and second terminal sequences is in a range of 3-10 base pairs.

5. The nucleic acid cleavage complex of claim 1, wherein the first terminal sequence of the polynucleotide chain is connected to the nanoparticle by thioether.

6. The nucleic acid cleavage complex of claim 1, wherein the target nucleic acid is a single-stranded RNA or a double-stranded DNA.

7. The nucleic acid cleavage complex of claim 1, wherein the nanoparticle is a gold nanorod or a core-shell nanoparticle.

8. A method of using a nucleic acid cleavage reagent, comprising the following steps:
   (a) providing a target nucleic acid and a nucleic acid cleavage complex, wherein said nucleic acid cleavage complex comprises:
      a nanoparticle;
      a nucleic acid cleavage reagent, wherein said nucleic acid cleavage reagent is photo-exiteable by visible light, ultraviolet light, and near infrared; and
      a polynucleotide chain which has a first terminal sequence and a second terminal sequence opposite to the first terminal sequence, wherein the first terminal sequence is connected to the nanoparticle, the second terminal sequence is connected to the nucleic acid cleavage reagent, and the first terminal sequence and the second terminal sequence are base-paired to make the polynucleotide chain form a hairpin;
   (b) allowing the nucleic acid cleavage complex to contact the target nucleic acid, wherein the polynucleotide chain of the nucleic acid cleavage complex specifically recognizes the sequence of the target nucleic acid; and
   (c) activating the nucleic acid cleavage reagent of the nucleic acid cleavage complex to cleave the sequence of the target nucleic acid.

9. The method as claimed in claim 8, wherein the average particle size of the nanoparticle is in a range of 1-100 nm.

10. The method as claimed in claim 8, wherein the length of the polynucleotide chain is in a range of 10-30 nucleotides.

11. The method as claimed in claim 8, wherein the length of the base-paired sequences between the first and second terminal sequences is in a range of 3-10 base pairs.

12. The method as claimed in claim 8, wherein the first terminal of the polynucleotide chain is connected to the nanoparticle by thioether.

13. The method as claimed in claim 8, wherein the target nucleic acid is a single-stranded RNA or a double-stranded DNA.

14. The method as claimed in claim 8, wherein the nanoparticle is a gold nanorod or a core-shell nanoparticle.

* * * * *